(12) United States Patent
Ernst et al.

(10) Patent No.: US 6,319,909 B1
(45) Date of Patent: Nov. 20, 2001

(54) LIQUID IODOPHOR FROM POLY-N-VINYL LACTAM, DEXTRIN AND ALCOHOLS

(75) Inventors: Andreas Ernst, Worms; Jörg Breitenbach, Mannheim; Axel Sanner, Frankenthal, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/403,637
(22) PCT Filed: Apr. 17, 1998
(86) PCT No.: PCT/EP98/02280
  § 371 Date: Oct. 25, 1999
  § 102(e) Date: Oct. 25, 1999
(87) PCT Pub. No.: WO98/47373
  PCT Pub. Date: Oct. 29, 1998

(30) Foreign Application Priority Data

Apr. 24, 1997 (DE) .............................. 197 17 191

(51) Int. Cl.$^7$ .................... A61K 31/715; A01N 25/00
(52) U.S. Cl. .............................. 514/58; 424/405
(58) Field of Search ................ 514/58; 424/405

(56) References Cited

U.S. PATENT DOCUMENTS

| 4,151,275 | 4/1979 | Cantor et al. ............... 424/80 |
| 4,197,318 * | 4/1980 | Sipos ..................... 424/326 |
| 4,684,519 | 8/1987 | Barabas ................... 424/80 |
| 5,731,009 | 3/1998 | Breitenbach et al. ........... 424/672 |
| 5,916,882 * | 6/1999 | Jeng ...................... 514/57 |

FOREIGN PATENT DOCUMENTS

| 2181933 | 2/1997 | (CA) . |
| 3819498 | 12/1988 | (DE) . |
| 107277 | 5/1984 | (EP) . |
| 172984 | 3/1986 | (EP) . |
| 342269 | 11/1989 | (EP) . |
| 526800 | 2/1993 | (EP) . |
| 756820 | 2/1997 | (EP) . |
| 95/28841 | 11/1995 | (WO) . |

OTHER PUBLICATIONS

Database EPODOC XP 002076308 (abstract of CN 1073577, Dec. 23, 1991).

* cited by examiner

Primary Examiner—Kathleen Kahler Fonda
(74) Attorney, Agent, or Firm—Keil & Weinkauf

(57) ABSTRACT

A process for preparing liquid iodophores with poly-N-vinyllactams and dextrins as carrier materials, which comprises heating a mixture of the carrier materials, iodine and iodide ions or, in place of the iodide ions, a reducing agent in aqueous medium in the presence of a monohydric or polyhydric alcohol having 1 to 6 carbon atoms at from 40 to 100° C.

3 Claims, No Drawings

LIQUID IODOPHOR FROM POLY-N-VINYL LACTAM, DEXTRIN AND ALCOHOLS

This application is a U.S. National Stage entry under 35 U.S.C. §371 of PCT/EP98/02280, filed Apr. 17, 1998.

The invention relates to an improved process for preparing a liquid iodophore with dextrin and a poly-N-vinyllactam as carrier material.

In the area of skin-safe disinfectants, PVP-iodine is a long-established product which is, however, costly. The preparation of saccharide-containing iodophores by polymerizing vinylpyrrolidone in the presence of the particular oligo- or polysaccharides is moreover disclosed in EP-A-526 800. Although products of this type are less costly than PVP-iodine, they do not comply with the requirements to be met by PVP-iodine. In addition, they have not to date been pharmacologically accepted.

WO 9528841 describes the preparation of iodophores from poly-N-vinyllactam and dextrin. For applications of the iodophore in liquid form, it is more expedient, simple and economic to carry out the process described in WO 9528841 in aqueous solution. However, preparation in pure aqueous solution results in highly viscous suspensions with a high solids content. An additional fault is the formation of iodine sublimate which may be observed. If, for example, a mixture of 10% by weight of polyvinylpyrrolidone (K value 30), 15% by weight of dextrin with a DE value of 17 to 19, 6% by weight of iodine, 0.3% by weight of ammonium formate and 68.7% by weight of water is heated with stirring over the course of four hours to 80° C., and after a further eight hours at 80° C., cooled to room temperature, the result is a highly viscous suspension (viscosity: 12300 mPas, see below for measurement) with 0.5% by weight of iodine sublimate and about 10% by weight of solid residue. The large amount of iodine-containing residue, the iodine sublimate and the pasty consistency of the resulting product make it appear desirable to find an improved process.

It is an object of the present invention to develop an improved process for the direct preparation of an iodophore solution with poly-N-vinyllactam and dextrin as carriers.

We have found that this object is achieved by a process for preparing liquid iodophores with poly-N-vinyllactams and dextrins as carrier materials, which comprises heating the carrier materials, iodine and iodide ions or, in place of the iodide ions, a reducing agent in aqueous medium in the presence of a monohydric or polyhydric alcohol having 1 to 6 carbon atoms at from 40 to 100° C.

Suitable monohydric or polyhydric alcohols according to the invention are methanol, preferably ethanol, n-propanol, n-butanol, n-pentanol, n-hexanol, isopropanol, isobutanol and other branched homologs of said alcohols, ethylene glycol, glycerol or mixtures thereof, with n-propanol being particularly preferred.

The iodophore is prepared by mixing the components and heating them at from 40 to 100, preferably 60 to 95° C. In a preferred variant of the process, the iodine is dissolved in the monohydric or polyhydric alcohol component and added dropwise. The reaction takes from 1 to 30 hours, depending on the amounts employed.

The liquid iodophores have the following composition in particular:
a) 5–60% by weight of polyvinylpyrrolidone or poly-N-vinylcaprolactam,
b) 5–60% by weight of dextrin with a DE value of from 2 to 40,
c) 1–30% by weight of elemental iodine,
d) 0.5–15% by weight of iodide ions,
e) 5–40% by weight of the alcohol component and
f) 20–80% by weight of water,
where the total of components a) to f) equals 100% by weight. Preferred iodophores have a viscosity <1000 mPa.s (25° C.), with a solids content of 25–40% by weight and an available iodine content of 10–18% by weight.

The dextrins are commercially available and can easily be obtained from starch by incomplete hydrolysis with dilute acid, by exposure to heat and by oxidative or enzymatic degradation using amylases.

Starch degradation products obtainable by hydrolysis in aqueous phase and having a weight average molecular weight of from 2500 to 25000 are, in distinction from the torrefaction dextrins, normally referred to as saccharified starches and are commercially obtainable as such.

Saccharified starches of this type differ chemically from the torrefaction dextrins inter alia in that on hydrolytic degradation in aqueous medium (normally suspensions or solutions), which is usually carried out with solids contents of from 10 to 30% by weight and preferably with acid or enzyme catalysis, there is essentially no possibility of recombination and branching, which is manifested not least by different molecular weight distributions.

The preparation of saccharified starches is generally known and is described, inter alia, in Günther Tegge, Stärke und Stärkederivate, Behr's Verlag, Hamburg 1984, page 173 and pages 220 ff, and in EP-A 441 197. The saccharified starches to be used according to the invention are preferably those whose weight average molecular weight $M_w$ is in the range from 4000 to 16000, particularly preferably in the range from 6500 to 13000.

The saccharified starches to be used according to the invention are normally completely stable in water at room temperature, with the solubility limit usually being above 50% by weight. It is preferred for 10 to 20% by weight, particularly preferably 30 to 40% by weight, solutions to be clear solutions, and not colloidal suspensions, at room temperature.

It is furthermore advisable to employ those saccharified starches to be used according to the invention whose dextrose equivalent DE is from 2 to 40, preferably 10 to 30 and particularly preferably 10 to 20. The DE value characterizes the reducing capacity relative to the reducing capacity of anhydrous dextrose and is determined as specified in DIN 10 308, edition 5.71, of the Deutscher Normenausschuss Lebensmittel und landwirtschaftliche Produkte (cf. also Günther Tegge, Stärke und Stärkederivate, Behr's Verlag, Hamburg 1984, page 305).

Suitable initial starches for preparing the saccharified starches to be used according to the invention are, in principle, all natural starches such as cereals starches (eg. corn, wheat, rice or millet), tuber and root starches (eg. potatoes, cassava roots or arrowroot) or sago starches.

It is a considerable advantage of the saccharified starches to be used according to the invention that, apart from the partial hydrolysis of the initial starch, which can be carried out in a very simple manner, no further chemical modification is required to prepare them for use.

The saccharified starches used in the Examples were the C* PUR products 01906, 01908, 01910, 01915, 01921, 01924, 01932 or 01934 of Cerestar Deutschland GmbH, Krefeld. They all have essentially a bimodal molecular weight distribution and have the following characteristics:

| Type | $M_w$ | H | % by weight <1000 | DE |
|---|---|---|---|---|
| 01906 | 20080 | 10.9 | 12.2 | 2–5 |
| 01908 | 19290 | 10.0 | 15.9 | 8–10 |
| 01910 | 10540–12640 | 8.5–9.9 | 24.7–26.4 | 11–14 |
| 01915 | 6680–8350 | 6.8–8.4 | 32.9–34.7 | 17–19 |
| 01921 | 6700 | 7.4 | 39.1 | 20–23 |
| 01924 | 4730 | 6.8 | 53.6 | 26–30 |
| 01932 | 4500 | 7.9 | 63.2 | 33–35 |
| 01934 | 3000 | 6.0 | 68.4 | 36–39 |

Determinations of $M_n$ by vapor pressure osmosis gave the following results for the preferred types 01910 and 01915:

1560 g/mol (1910)

980 g/mol (1915)

H=heterogeneity $M_w$=weight average molecular weight $M_n$=number average molecular weight DE=dextrose equivalent To react the iodine and iodide with the carrier in solution, the iodine must be present in homogeneous form. The complex is formed by adding sufficient iodine and iodide for the final mixture to contain from 1 to 30, preferably 1 to 10, % by weight of iodine and 1 mol of iodide per mole of iodine ($I_2$). The cation of the iodide is immaterial and is usually sodium or potassium. The iodide can be replaced by an equivalent amount of a reducing agent which reduces iodine to iodide, for example formic acid and its salts, preferably ammonium formate, glucose, ascorbic acid, malonic acid, oxalic acid, ammonium oxalate, if the initial amount of iodine is increased correspondingly. It must be taken into account in this connection that dextrins also have a certain iodine-reducing capacity because of their aldehydic end groups. It has emerged, surprisingly, that it was possible to obtain, by adding low alcohols, preferably ethanol or propanol, as solvents for the iodine, and preferably ethylene glycol or glycerol as phase compatibilizer for the carrier materials, a homogeneous, low-viscosity solution, during and after the several hours of heating, which additionally showed no iodine sublimation. The results without addition of alcohols are highly viscous mixtures with varying amounts of insoluble solids which evidently consist of iodine and polymeric material and/or incompatibilities between the carrier materials (phase separations) and, in addition, iodine sublimate.

The improved solution can be marketed and used as such. The solution can moreover be used as skin-safe disinfectant or for disinfecting instruments and surfaces as dilute solution. The product is miscible, and can be diluted, with water in any ratio.

The poly-N-vinyllactams have K values as specified by H. Fikentscher (Cellulosechemie 13 (1932), 58–64 and 71–74) in the range from 12 to 100, preferably 25 to 70. Particularly suitable poly-N-vinyllactams are poly-N-vinylpyrrolidone (PVP) or poly-N-vinylcaprolactam. PVP is particularly preferred.

The available iodine content is determined as specified in the Deutsches Arzneimittel Codex (DAC) 1986, 2nd supplement 1990, for polyvidone-iodine. The specification for available iodine content therein is from a minimum of 9 to a maximum of 12%. The same applies to USP XXII (Povidone-Iodine). Determination of the iodide content is also described therein. The available iodine content corresponds to the value which can be measured by thiosulfate titration. The free iodine content is determined by the method of D. Horn and W. Ditter "PVP-Iod in der operativen Medizin", pages 7 et seq., Springer-Verlag, Heidelberg 1984.

The loss of available iodine (iodine loss) on high-temperature storage provides information on the stability of the complex and is determined as follows:

Determination takes place on a PVP-iodine solution containing 1% available iodine.

High-temperature Storage

A brown 25 ml bottle with ground glass stopper is filled to 1 cm below the stopper with PVP iodine solution and then stored in an oven at 80° C.±0.5° C. for 15 hours. The bottle is briefly ventilated by lifting the stopper about 15 minutes after its introduction into the oven. After storage for 15 hours and after the contents of the bottle have cooled, 5.0 ml are removed and the available iodine content is determined as described in DAC using 0.02 N sodium thiosulfate solution (amount used N).

Calculation of the iodine loss $$\% \text{ iodine loss} = \frac{V * N}{1} \cdot 100$$

where:

V=ml of $Na_2S_2O_3$* solution used before storage

N=ml of $Na_2S_2O_3$* solution used after storage

Note

In order to be able to detect irregularities (temperature fluctuations, loss of power etc.) during storage, it is expedient also to analyze a comparison sample with a known iodine loss.

Viscosity Determination

The viscosity of the resulting products was measured using a Rotavisco RV 20 rotational viscometer with an M measuring system supplied by HAAKE Mess-Technik GmbH (Karlsruhe, Germany).

All measurements took place at 25° C. The dynamic viscosity is reported in mPas.

The dextrins are not on their own able to form adequately stable iodine complexes. However, they can do this when mixed with PVP or poly-N-vinylcaprolactam since equal amounts of the mixture on the one hand and of unmixed PVP or poly-N-vinylcaprolactam on the other hand take up identical amounts of iodine, in fact with the same binding power. Thus there is evidently a type of synergism in the mixture. In contrast to graft copolymers, the mixtures are pharmacologically accepted products. Compared with PVP-iodine, the iodophores have not only ecological advantages deriving from the good biodegradability of the dextrin content, but also economic advantages, because the costs of the starting materials are substantially reduced.

The liquid iodophore according to the invention is expedient and particularly well suited, because of its easy dispersibility in water, for applications of iodophores in aqueous systems. In addition, it is unnecessary to dry the aqueous solutions of poly-N-vinyllactam and dextrin resulting from the preparation. It was surprisingly possible by adding lower alcohols to obtain low-viscosity solutions which contained neither iodine sublimate nor insoluble residues. The invention thus provides in a surprisingly simple manner an economic and simple way of obtaining liquid iodophores in the form of aqueous solutions.

EXAMPLES

1. A mixture of 12% by weight of polyvinylpyrrolidone (K value 30), 12% by weight of dextrin with a DE value of 17 to 19, 6% by weight of iodine, 0.3% by weight of ammonium formate, 16.7% by weight of ethanol and 53% by weight of water was heated with stirring to 80° C. over the course of four hours. After a further eight hours at 80° C., the solution was cooled to room temperature. The theoretical solids content is 30% by weight. The available iodine content based on solids was 13.9%, the iodine loss was 5.7%, the free iodine content was 4.1 ppm, the iodide content was 6.4% and the viscosity was 120 mPas.

2. A mixture of 12% by weight of polyvinylpyrrolidone (K value 30), 12% by weight of dextrin with a DE value of 17 to 19, 6% by weight of iodine, 0.3% by weight of ammonium formate, 16.7% by weight of n-propanol and 53% by weight of water was heated with stirring to 80° C. over the course of four hours. After a further eight hours at 80° C., the solution was cooled to room temperature. The theoretical solids content is 30% by weight. The available iodine content based on solids was 13.6%, the iodine loss was 8.3%, the free iodine content was 5.2 ppm, the iodide content was 6.0% and the viscosity was 148 mPas.

3. A mixture of 21% by weight of polyvinylpyrrolidone (K value 30), 3% by weight of dextrin with a DE value of 17 to 19, 6% by weight of iodine, 0.3% by weight of ammonium formate, 15% by weight of i-propanol and 54.7% by weight of water was heated with stirring to 80° C. over the course of four hours. After a further eight hours at 80° C., the solution was cooled to room temperature. The theoretical solids content is 30% by weight. The available iodine content based on solids was 11.0%, the iodine loss was 10.1%, the free iodine content was 2.2 ppm, the iodide content was 5.8% and the viscosity was 80 mPas.

4. A mixture of 9% by weight of polyvinylpyrrolidone (K value 30), 12% by weight of dextrin with a DE value of 17 to 19, 6% by weight of iodine, 0.3% by weight of ammonium formate, 20% by weight of glycerol, 10% by weight of ethanol and 42.7% by weight of water was heated with stirring to 80° C. over the course of four hours. After a further eight hours at 80° C., the solution was cooled to room temperature. The theoretical solids content is 27% by weight. The available iodine content based on solids was 13.2%, the iodine loss was 5.5%, the free iodine content was 8.2 ppm, the iodide content was 6.2% and the viscosity was 420 mPas.

5. A mixture of 24% by weight of polyvinylpyrrolidone (K value 30), 0% by weight of dextrin with a DE value of 17 to 19, 6% by weight of iodine, 0.3% by weight of ammonium formate, 6% by weight of ethylene glycol, 10% by weight of ethanol and 53.7% by weight of water was heated with stirring to 80° C. over the course of four hours. After a further eight hours at 80° C., the solution was cooled to room temperature. The theoretical solids content is 30% by weight. The available iodine content based on solids was 12.7%, the iodine loss was 7.9%, the free iodine content was 6.3 ppm, the iodide content was 6.4% and the viscosity was 280 mPas.

6. A mixture of 12% by weight of polyvinylpyrrolidone (K value 30), 12% by weight of dextrin with a DE value of 17 to 19, 6% by weight of iodine, 0.3% by weight of ammonium formate, 14% by weight of n-propanol and 55.7% by weight of water was heated with stirring to 70° C. over the course of four hours. After a further eight hours at 70° C., the solution was cooled to room temperature. The theoretical solids content is 30% by weight. The available iodine content based on solids was 14.4%, the iodine loss was 10.5%, the free iodine content was 5.3 ppm, the iodide content was 7.0% and the viscosity was 110 mPas.

7. A mixture of 10.8% by weight of polyvinylpyrrolidone (K value 30), 13.2% by weight of dextrin with a DE value of 17 to 19, 6% by weight of iodine, 0.3% by weight of ammonium formate, 20% by weight of ethanol and 49.7% by weight of water was heated with stirring to 80° C. over the course of four hours. After a further eight hours at 80° C., the solution was cooled to room temperature. The theoretical solids content is 30% by weight. The available iodine content based on solids was 13.1%, the iodine loss was 12.5%, the free iodine content was 4.6 ppm, the iodide content was 6.6% and the viscosity was 145 mPas.

8. A mixture of 20% by weight of polyvinylpyrrolidone (K value 30), 4% by weight of dextrin with a DE value of 17 to 19, 6% by weight of iodine, 0.3% by weight of ammonium formate, 10.7% by weight of i-propanol and 59% by weight of water was heated with stirring to 80° C. over the course of four hours. After a further eight hours at 80° C., the solution was cooled to room temperature. The theoretical solids content is 30% by weight. The available iodine content based on solids was 11.0%, the iodine loss was 17.1%, the free iodine content was 2.1 ppm, the iodide content was 6.1% and the viscosity was 130 mPas.

9. A mixture of 25.5% by weight of iodine, 0.6% by weight of ammonium formate and 73.9% by weight of ethanol was added with stirring over the course of 30 min to a solution of 30% by weight of polyvinylpyrrolidone (K 30) and 70% by weight of water heated to 80° C. After a further 11 hours at 80° C., the solution was cooled to room temperature. The solids content was 29% by weight, the iodine loss was 9.0% by weight, the available iodine content was 11.6% by weight and the viscosity was 130 mPa.s at 25° C.

We claim:

1. A process for preparing liquid iodophores with poly-N-vinyllactams and dextrins as carrier materials, which comprises heating a mixture of the carrier materials, iodine and iodide ions or, in place of the iodide ions, a reducing agent, in aqueous medium in the presence of a monohydric or polyhydric alcohol having 1 to 6 carbon atoms at from 40 to 100° C.

2. A process as claimed in claim 1, wherein n-propanol is employed as alcohol component.

3. A process as claimed in claim 1, wherein the iodine is dissolved in the alcohol component and added dropwise to an aqueous solution of the other components.

* * * * *